(12) United States Patent
Densham

(10) Patent No.: US 7,604,963 B2
(45) Date of Patent: Oct. 20, 2009

(54) METHOD FOR SEQUENCING NUCLEIC ACID MOLECULES

(75) Inventor: Daniel Densham, Exeter (GB)

(73) Assignee: Medical Biosystems Ltd (GB)

( * ) Notice: Subject to any disclaimer, the term of this patent is extended or adjusted under 35 U.S.C. 154(b) by 0 days.

(21) Appl. No.: 10/565,750

(22) PCT Filed: Jul. 26, 2004

(86) PCT No.: PCT/GB2004/003232

§ 371 (c)(1),
(2), (4) Date: Feb. 28, 2007

(87) PCT Pub. No.: WO2005/010210

PCT Pub. Date: Feb. 3, 2005

(65) Prior Publication Data

US 2008/0070236 A1    Mar. 20, 2008

(30) Foreign Application Priority Data

Jul. 24, 2003    (GB) ................................. 0317343.2

(51) Int. Cl.
*C12P 19/34* (2006.01)
*C12Q 1/68* (2006.01)
*C07H 21/00* (2006.01)
*C07H 21/02* (2006.01)

(52) U.S. Cl. ................. 435/91.1; 435/6; 435/91.2; 536/24.3; 536/24.33

(58) Field of Classification Search ............... 435/6, 435/91.1, 91.2; 536/24.3, 24.33
See application file for complete search history.

(56) References Cited

U.S. PATENT DOCUMENTS 6,174,670 B1 *    1/2001   Wittwer et al. ................ 435/6

FOREIGN PATENT DOCUMENTS

| CN | 1245218 | 2/2000 |
|----|---------|--------|
| WO | WO 99/05315 | 2/1999 |
| WO | WO 00/53805 | 9/2000 |
| WO | WO 00/70073 | 11/2000 |
| WO | WO 03/027326 | 4/2003 |

* cited by examiner

*Primary Examiner*—Jezia Riley
(74) *Attorney, Agent, or Firm*—Saliwanchik, Lloyd & Saliwanchik

(57) ABSTRACT

The sequence of a target polynucleotide can be determined by: (i) contacting the target polynucleotide with a polymerase enzyme and one of the nucleotides A, T(U), G, and C under conditions suitable for the polymerase reaction to proceed; (ii) measuring the time taken for the polymerase to bind to and subsequently dissociate from the target polynucleotide, to thereby determine whether the polymerase has incorporated the nucleotide onto the target polynucleotide; (iii) optionally repeating steps (i) and (ii) with additional nucleotides, to thereby identify the sequence of the target polynucleotide.

19 Claims, 2 Drawing Sheets

SEQUENCE LISTING

<160> NUMBER OF SEQ ID NOS: 2

<210> SEQ ID NO 1
<211> LENGTH: 53
<212> TYPE: DNA
<213> ORGANISM: Artificial Sequence
<220> FEATURE:
<223> OTHER INFORMATION: target polynucleotide

<400> SEQUENCE: 1
caaggagagg acgctgcttg tcgaaggtaa ggaacggacg agagaaggga gag        53

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
ctctcccttc tctcgtc        17

METHOD FOR SEQUENCING NUCLEIC ACID MOLECULES

CROSS-RFERENCE TO RELATED APPLICATION

This application is the National Stage of International Application Number PCT/GB2004/003232, filed Jul. 26, 2004, which is hereby incorporated by reference herein in its entirety, including any figures, tables, nucleic acid sequences, amino acid sequences, or drawings.

FIELD OF THE INVENTION

The present invention relates to methods for determining the sequence of a polynucleotide or detecting variations between polynucleotide sequences.

BACKGROUND TO THE INVENTION

The ability to determine the sequence of a polynucleotide is of great scientific importance, as demonstrated by the Human Genome Project, which has now determined the entire sequence of the three billion bases of the human genome. However, this sequence information represents an average human and there is a considerable need to understand the differences between individuals at a genetic level.

The principal method in general use for large-scale DNA sequencing is the chain termination method. This method was first developed by Sanger and Coulson (Sanger et al. Proc. Natl. Acad. Sci. USA 1977; 74: 5463-5467), and relies on the use of dideoxy derivatives of the four nucleoside triphosphates which are incorporated into the nascent polynucleotide chain in a polymerase chain reaction. Upon incorporation, the dideoxy derivatives terminate the polymerase reaction and the products are then separated by gel electrophoresis and analysed to reveal the position at which the particular dideoxy derivative was incorporated into the chain.

Although this method is used widely and produces reliable results, it is recognised that it is slow, labour-intensive and expensive. Furthermore, it is not an effective method for detecting the differences between two sequences, which may often consist of a single base change (known as a Single Nucleotide Polymorphism, or SNP).

Nucleic acid arrays have recently become a preferred method of determining polynucleotide sequences and SNPs, usually in the context of hybridisation events (Mirzabekov, Trends in Biotechnology (1994) 12:27-32). A large number of array-based sequencing procedures utilise labelled nucleotides in order to obtain the identity of the added (hybridised) bases. These arrays rely on the stepwise identification of suitably labelled bases, referred to in U.S. Pat. No. 5,634,413 as "single base" sequencing methods. Such "single base" procedures utilise two types of label; the radiolabel and the fluorescent label. The radiolabelling of nucleotides has the advantages of high sensitivity and low background. However, radiolabelling suffers from poor resolution.

Fluorescently-labelled nucleotides are now used widely in many techniques. Such nucleotides can be incorporated into the nascent polynucleotide chain in a stepwise manner by the polymerase chain reaction. Each of the different nucleotides (A, T. G and C) incorporates a unique fluorophore at the 3' position which can be detected using a sensitive fluorescent detector, e.g. a charge-coupled detector (CCD). The fluorophore often also acts as a "blocking group", which removes the ability of the incorporated nucleotide to serve as a substrate for further nucleotide addition and therefore prevents uncontrolled polymerisation. Often, a "removable blocking group" is used, which can be removed by a specific treatment that results in cleavage of the covalent bond between a nucleotide and the blocking group, allowing the sequencing reaction to continue.

Removable blocking groups rely on a number of possible removing treatment strategies, for example, a photochemical, chemical or enzymatic treatment. However, these have been shown to be difficult to control and apply. Differences in local environments, for example within an array, can result in the removal of an entire nucleotide, or even several nucleotides, instead of just the intended label. Such occurrences have serious consequences for the fidelity of the sequencing method, as uncontrolled removal of nucleotides results in sequencing data becoming out of phase and sequence data becoming corrupted or unusable.

A further disadvantage of both labelling methods is that repeat sequences can lead to ambiguity of results. This problem is recognised in Automation Technologies for Genome Characterisation, Wiley-Interscience (1997), ed. T. J. Beugelsdijk, Chapter 10:205-225.

There is therefore a need for an improved method for identifying the sequence of a polynucleotide, in particular for detecting variations within a polynucleotide sequence, eg for detecting SNPs, which combines the high sensitivity and low background of radiolabelled nucleotides with the high resolution of fluorescently-labelled labels. Further, the method should be capable of being carried out by high-throughput, automated processes, reducing the cost associated with existing methods.

SUMMARY OF THE INVENTION

The present invention is based on the realisation that the identification of a polynucleotide sequence can be carried out by measuring the time during which a polymerase binds to a target polynucleotide during a polymerase reaction. In general, a polymerase will spend less time bound to the target polynucleotide when there is no nucleotide available for incorporation. Therefore, if the only nucleotide available is non-complementary, the polymerase will bind to the polynucleotide for a shortened period, and this can be determined to reveal the identity of the complementary sequence of the target polynucleotide.

According to a first aspect of the present invention, a method of identifying the sequence of a polynucleotide comprises:

(i) contacting the target polynucleotide with a polymerase enzyme and one of the nucleotides A, T(U), G and C under conditions suitable for the polymerase reaction to proceed;

(ii) measuring the time taken for the polymerase to bind to and subsequently dissociate from the target polynucleotide, to thereby determine whether the polymerase has incorporated the nucleotide onto the target polynucleotide; and (iii) optionally repeating steps (i) and (ii) with additional nucleotides, to thereby identify the sequence of the target polynucleotide.

According to a second aspect of the present invention, a method for the identification of a mutation in a target polynucleotide, comprises the steps of:

(i) contacting the target polynucleotide with a polymerase enzyme and one of the nucleotides A, T (U), G and C under conditions suitable for the polymerase reaction to proceed; and (ii) measuring the time taken for the polymerase to bind to and subsequently dissociate from the target polynucleotide, to thereby identify whether the polymerase has incorporated the nucleotide onto the target polynucleotide, and with reference to the native sequence of the target, determine whether a mutation exists.

DESCRIPTION OF THE INVENTION

Figure 1A:
FIGS. 1A and 1B show time-resolved CCD images of a sequencing reaction using complementary nucleotide (FIG. 1A) or non-complementary nucleotide (FIG. 1B).

The term "polynucleotide" or "target polynucleotide" as used herein is to be interpreted broadly, and includes DNA and RNA, including modified DNA and RNA, as well as other hybridising nucleic acid-like molecules e.g. peptide nucleic acid (PNA). The target polynucleotide may be double or single-stranded. Preferably, the target polynucleotide is at least partially single-stranded and more preferably has a primer sequence bound to it, such that the polymerase enzyme can attach to the target polynucleotide, as will be appreciated by one skilled in the art.

The enzyme is a polymerase enzyme, which interacts with the target polynucleotide in the process of extending a complementary strand, and may be of any known type. For example, the polymerase may be any DNA-dependent DNA polymerase. If the target polynucleotide is a RNA molecule, then the polymerase may be an RNA-dependent DNA polymerase, i.e. reverse transcriptase, or a RNA-dependent RNA polymerase, i.e. RNA replicase. Primase enzymes are also included within the definition.

The target polynucleotide is preferably localised at a specific site on a support material. Preferably, the polynucleotide is localised via immobilisation on a solid support. Supports suitable for use in immobilising the polynucleotide will be apparent to the skilled person, for example silicon, glass or ceramic materials may all be used. Immobilisation may be carried out by covalent or non-covalent means. For example, covalent linker molecules may be used. In a preferred embodiment, a primer is immobilised onto the support material and the target polynucleotide is hybridised to it. Alternatively, hybridisation of the target polynucleotide and primer may take place in solution and either the primer or target polynucleotide is subsequently, or simultaneously, attached to a support material.

There may be one or more target polynucleotides immobilised to the solid support material. In a preferred embodiment, a plurality of target polynucleotides are attached to the support. These "arrays" of target polynucleotides may be of any known density, including multi-molecule, high-density arrays as well as "single-molecule" arrays in which individual polynucleotide locations may be resolved, i.e. it is possible to monitor the polymerase reaction occurring on a single polynucleotide.

As a first step in the sequencing method, the target polynucleotide may be brought into contact with an appropriate primer in hybridising/polymerisation buffer. Typically, the buffer will be at a temperature sufficiently high to disrupt (or melt) any secondary structures that exist on the target polynucleotide. On cooling, the primer will anneal to its complement on the target. This is then brought into contact with the polymerase, to form the target polynucleotide/polymerase complex.

In one embodiment of the invention, the addition of the nucleotides is controlled so that the different nucleotides are added sequentially to the polymerase/target complex. For example, dGTP may be added and allowed to flow over the polymerase/polynucleotide complex; the time during which the polymerase is complexed to the polynucleotide is then determined. Unbound dGTP flows out of the reaction site and a further nucleotide is introduced. In this manner, the time during which the complex is formed can be correlated to the particular nucleotide present during that time and the polynucleotide sequence, can therefore be determined.

The reaction may also be started by the addition of the polymerase to a reaction mixture which comprises the target polynucleotide and the nucleotide. After monitoring the time taken by the polymerase to associate with and dissociate from the target polynucleotide, the unbound nucleotides can be removed and the next nucleotide introduced to carry out further sequencing steps.

The incorporation of a nucleotide onto the target requires the polymerase to associate with the target for a period longer than that taken when no incorporation is possible. Measurement of the association between the polymerase and the target therefore reveals whether an incorporation event has occurred for regions on the target having sequential nucleotides of the same type, the time of association will increase proportionally. Therefore the method can be used to identify consecutive nucleotides of the same type.

The detection of the interaction between the polymerase enzyme and the target polynucleotide can be carried out by measuring changes in applied radiation. Measuring the changes in radiation that occurs on interaction between the polymerase and target polynucleotide may be carried out using conventional apparatus.

In one embodiment, the interaction of the polymerase with the target polynucleotide is measured using a non-linear imaging system.

Non-linear imaging systems are known in the art. In general, the non-linear polarisation for a material can be expressed as:

$$P = X^{(2)}E^1 + X^{(2)}E^2 + X^{(3)}E^3 + \ldots$$

where P is the induced polarisation, $X^{(n)}$ is the nth-order non-linear susceptibility, and E is the electric field vector. The first term describes normal absorption and reflection of light; the second describes second harmonic generation (SHG), sum and difference frequency generation; and the third describes light scattering, stimulated Raman processes, third harmonic generation (TGH), and both two- and three-photon absorption.

A preferred imaging system of the present invention relies on the detection of the signal arising from second or third harmonic generation.

Single-molecule resolution using second or third harmonic generation (hereinafter referred to as SHG) is known in the art (Peleg et al., Proc. Natl. Acad, Sci. USA, 1999;95:6700-6704 and Peleg et al., Bioimaging, 1996; 4:215-224). Suitable systems are described in WO-A-02/095070.

In one embodiment, detection is carried out in solution phase (i.e. the polymerase and target polynucleotide are not immobilised), using raman scattering and/or LSPR techniques.

When light is directed onto a molecule, the vast majority of the incident photons are elastically scattered without a change in frequency. This is termed Rayleigh scattering. However, the energy of some of the incident photons (approximately 1 in every $10^7$ photons) is coupled into distinct vibrational modes of the molecule's bonds. Such coupling causes some of the incident light to be inelastically scattered by the molecule with a range of frequencies that differ from the range of the incident light. This is termed the Raman effect. By plotting the frequency of such inelastically scattered light against intensity, the unique Raman spectrum of the molecule under investigation is obtained. Analysis of the Raman spectrum of an unknown sample can yield information about the samples molecular composition.

The Raman effect can be enhanced significantly by bringing the Raman active molecule(s) close ($\leq$50 Å) to a structured metal surface, this field decays exponentially away from the surface. Bringing molecules in close proximity to metal surfaces is typically achieved through adsorption of the Raman-active molecule onto suitably roughened gold, silver copper or other free-electron metals. Surface enhancement of the Raman activity is observed with metal colloidal particles, metal films on dielectric substrates, and with metal particle arrays. The mechanism by which this surface-enhanced Raman scattering takes place is not well understood, but it thought to result from a combination of (i) surface plasmon resonances in the metal that enhance the local intensity of the light, and; (ii) formation and subsequent transitions of charge-transfer complexes between the metal surface and the Raman-active molecule.

The Raman effect can be utilised to measure the time of association between the polymerase and the target polynucleotide. It is preferred if the target is immobilised on a metal surface, to improve the Raman signal.

In a preferred embodiment of the present invention, Surface Enhanced Raman Scattering (SERS) is employed via the use of a metal colloidal nanoparticle bound to the polymerase eg. a gold or silver nanoparticle. A Raman enhancing metal nanoparticle that has associated or bound to it a Raman-active molecule(s) can have utility as an optical tag. This general concept is outlined in U.S. Pat. No. 6,514,767, the content of which is hereby incorporated by reference. In one embodiment, the target polynucleotide and a polymerase can be detected by searching the Raman active molecule's unique raman spectrum. Because a single Raman spectrum (from 100-3500 cm−1) can detect many different Raman-active molecules, SERS-active nanoparticles bound to or associated with the polymerase may be used in the context of the present invention within multiplexed assay formats.

In a separate embodiment, changes in radiation are monitored by utilising surface electromagnetic wave technology.

Biosensors incorporating surface electromagnetic wave technology (and, in particular, surface plasmon resonance—SPR—sensors) are based on the sensitivity of surface electromagnetic waves (SEW) to the refractive index of the thin layer adjacent to the surface where the SEW propagates. In the biosensor, the polymerase and nucleotide(s) are allowed to flow across the surface containing the immobilised target polynucleotide. As binding occurs, the accumulation or redistribution of mass on the surface changes the local refractive index that can be monitored in real time by the sensor.

Several methods utilising SPR technology have been proposed and realised in biosensors. The most popular methods are based on the Kretschmann-Raether configuration where the intensity of the light reflected from the sensor is monitored. This technique, considered to be one of the most sensitive, is described in J. Homola et al, Sensors and Actuators B 54, p. 3-15 (1999) and has a detection limit of $5\times10^{-7}$ refractive index units. Measuring SPR phase changes can further increase the sensitivity of the sensor by one or two orders of magnitude. This is described in Nelson et al, Sensors and Actuators B 35-36, p. 187 (1996) and in Kabashkin et al, Optics Communications 150, p. 5 (1998). Prior art interferometric devices such as a Mach Zehnder device have been configured to measure variations in the refractive index at the sensor surface via phase shifts. This is disclosed in International Patent Publication WO-A-0120295. The configuration requires four independent components and is sensitive to sub-wavelength relative replacements of these components and hence very small mechanical and environment pertubations. A mechanically more robust monolithic interferometric design is oulined in WO-A-03014715.

In a preferred embodiment, a surface electromagnetic wave (SEW) sensor system is used which can compensate for changes in the bulk refractive index of a buffer or which allows the contribution of the bulk refractive index to an interference pattern to be separated from the contribution of an analyte absorbed on the sensor surface. The biosensor therefore comprises:

a coherent radiation source for producing an incident wave;

a carrier surface for supporting the immobilised polynucleotide, the carrier surface mounted on a substrate and capable of supporting surface electromagnetic waves (SEW);

means for splitting the incident wave into an SEW and a first scattered wave, wherein the SEW propagates along the carrier surface and interacts with the immobilised polynucleotide;

means for generating a second scattered wave from the SEW; and a detector for monitoring the interference between the first scattered wave and the second scattered wave.

In this embodiment, a coherent optical beam generated by a monochromatic laser is focussed using a lens, onto the edge of a metallic film able to support surface electromagnetic waves (SEWs). The optical beam passes through a glass prism on which the metallic film is mounted. A near-infrared laser is used as the illumination source. Using a near-infrared source has the advantage of long propagation length for surface plasmons in gold and silver while conventional optics can be still used for imaging and illumination. However, other monochromatic sources are suitable and may be used.

This system is described in WO-A-04/020985, the content of which is incorporated herein by reference.

In a preferred embodiment, the polymerase is labelled.

The term "label" as used herein may be interpreted broadly. Suitable labels will be apparent to the skilled person. In a preferred embodiment, the label is a fluorophore. In a particular embodiment, the polymerase is prepared as a recombinant fusion with GFP (Green Fluorescent Protein). This may either be wild type GFP or spectrally shifted mutants thereof (Tsien, Ann. Rev. Biochem., 1998; 67:509, U.S. Pat. No. 5,777,079 and U.S. Pat. No. 5,625,048). The GFP can be located at the N- or C-terminus of the enzyme (the C-terminus may be desirable if a polymerase is to be used in conjunction with a 'sliding clamp'). Alternatively, the GFP molecule may be located anywhere within the enzyme, provided that enzymatic activity is retained. Alternative labels may be used. A number of strategies for labelling molecules have been reported, such as microspheres (Anal. Chem. (2000) 72, 15:3678-3681), gold nanoparticles (J. Am. Chem. Soc. (2000) 122, 15:3795-3796), silver colloid particles (PNAS, (2000) 97, 3:996-1001) and quantum dots. Any labelling technique that allows unambiguous resolution of the interaction of the polymerase with the target polynucleotide and nucleotide can be utilised within the context of the present invention. Preferably, a label that allows the temporal resolution of enzyme binding and/or unbinding from the target polynucleotide:nucleotide complex is used.

Preferably, an array of immobilised target polynucleotides is created and the polymerase enzyme is flowed over the array in conditions sufficient for enzyme activity, together with at least one of the four nucleotides. More preferably, this takes place within a flow cell. Each "array location" within the array, containing a single immobilised target polynucleotide or plurality of identical target polynucleotides, is then imaged at a time resolution that allows resolution of the binding of the enzyme to the target polynucleotide/nucleotide complex, preferably, from 1 to at least several thousand hertz.

In another preferred embodiment, the polymerase enzyme is labelled with a Fluorescence Resonance Energy Transfer (FRET) pair. This system is described in WO-A-01/25480. As will be appreciated by one skilled in the art, a FRET pair requires a fluorophore and a second molecule that is capable of interacting with the fluorophore, acting as an energy donor or acceptor. The interaction between the pair alters the emission spectrum of the fluorophore(s), which is detected. The second molecule may be another fluorophore, or any other suitable molecule, such as a metallic particle. Preferably a classical FRET pair is used, where both labels are fluorophores, chosen so that the emission wavelength of one fluorophore corresponds to the excitation wavelength of the other. The immobilisation locations on the enzyme are chosen such that the fluorophores move relative to one another when the enzyme binds to the polynucleotide forming the ternary complex. This relative movement between the FRET pair will result in a spectral shift of the emission from the pair, depending upon the way in which the FRET pair has been designed. More or less energy is then coupled into the acceptor from the donor, leading to excitation or attenuation of the donor fluorescence. This is monitored with high temporal resolution, to obtain the desired information. Preferably the device used to image the extent of fluorescence is a charge-coupled device (CCD), with rapid read-out time and appropriate optics for high spatial resolution.

The resolution system required to monitor the interaction between the polymerase and the target can be modified to take into account the need to "scan" the sample under study. Such scanning is especially likely in high resolution systems, such as single molecule systems. At the high levels of spatial resolution required for single molecule experiments, the effective observation area is correspondingly reduced. Since "kinetic" analysis normally requires continuous "real-time" monitoring at a single defined area, scanning introduces the problem of discontinuous monitoring. Such discontinuous monitoring is incompatible with kinetic analysis as interaction events can be missed. In a preferred aspect of the present invention, therefore, nucleotides labelled at the 5 prime end are employed; the label acting as a removable blocking group Thus in situations where high spatial resolution is employed (such as single molecule arrays in which the observation region is typically only 100 μm by 100 μm and the chip is generally at least 100 times larger), the observation region is "moved" to a new location and that region illuminated with radiation (e.g. UV) suitable to remove the blocking group. This strategy ensures that association/kinetic events only occur in an "observed" region. The "observed" region can then be moved around the chip and by only exposing the region under observation to radiation sufficient to unblock the nucleotide, selective interactions only take place in this region.

In a further separate preferred embodiment imaging areas are confined to individual flow cells, i.e. in the event of the observation area being limited to 100 μm by 100 μm, the flow cell is restricted approximately to these relative dimensions. Thus, in this embodiment, nucleotides are only injected into flow cells that are being actively imaged. The support material onto which the polynucleotides are arrayed, may therefore consist of an "array" of individually addressable flow cells. As the imaging area is moved around the chip, so the nucleotides are injected into the flow cell(s) in the imaging area only.

In a further embodiment, the binding of the polymerase is detected via a resonance energy transfer between an intercalating molecule and a dye/quencher on the polymerase. The intercalating dye (e.g. CYBRGreen, molecular probes) will only fluoresce when binding to the double stranded primer-template complex. This signal can then be used to identify the location of the target polynucleotide. The polymerase is modified with a dye that is an "acceptor" molecule capable of absorbing and re-emitting energy from the intercalating dye. Alternatively, the "label" may be a quencher. Thus the binding/interaction event may be monitored by observing the change in signal due to energy transfer.

The method of the invention may be used to identify the complete target polynucleotide sequence, or may be used to identify the sequence of a part of the polynucleotide. The method is suitable for determining the presence of mutations within the target, for example determining whether a substitution, deletion or addition has occurred, compared to a control or reference sequence.

In a preferred embodiment, the method can be used to identify a single nucleotide polymorphism in a genetic sample. The term "polymorphism" as used herein refers to the occurrence of two or more alternative genomic sequences or alleles between or among different genomes or subjects. A single nucleotide polymorphism (SNP) is a single base pair change. Typically, a SNP is the replacement of one nucleotide by another nucleotide at the polymorphic site. Deletion of a single nucleotide, or insertion of a single nucleotide, also gives rise to single nucleotide polymorphisms.

The method is used to determine the identity of the nucleotide(s) at the putative site of mutation and the information may then be compared to a reference sequence to reveal whether a mutation is present.

The following Example illustrates the invention.

EXAMPLE

In this experiment, a fusion protein of Green Fluorescent Protein (GFP) and a polymerase was created via recombinant techniques well known in the art.

Quartz chips (14 mm in diameter, 0.3 mm thick) were spin-coated with a layer of planar dextran modified with immobilised streptavidin (Xantec, Germany). An upright microscope (135TV, Zeiss) equipped with total internal reflection (TIR) illumination served as a platform for the experiment. A laser beam of peak 488 nm (Melles Griot) with a power of 100 mW was circularly polarised by quarter-wave plates to undergo TIR in a custom made prism. The prism was coupled optically to the chip via index matching gel. A flow cell with an O-ring seal and transparent optical axis was then assembled over the prism and quartz chip. An objective collected the fluorescence signal through the transparent top surface of the flow cell. Images travelled via a band-pass filter into a back-thinned charge-coupled device (Andor technologies).

Two oligonucleotides were synthesized using standard phosphoamidite chemistry. The oligonucleoitde defined as SEQ ID NO.1 was used as the target polynucleotide, and the oligonucleoitde defined as SEQ ID NO.2 was biotinated and used as a primer. The biotinated primers (SEQ ID No.2) where deposited onto the streptavidin coated chip by injection into the flow cell 10 pM of SEQ ID NO.2 in Tris buffer containing 100 mM $MgCl_2$ and allowed to incubate for 10 minutes.

SEQ ID NO. 1
CAAGGAGAGGACGCTGCTTGTCGAAGGTAAGGAACGGACGAGAGAAGG
GAGAG

SEQ ID NO. 2
biotin-CTCTCCCTTCTCTCGTC

The flow buffer was flushed into the flow cell at a rate of 500 µl/min. The complementary sequence, SEQ ID NO.1 was then injected into the flow cell at a concentration of 1 µM, at a flow rate of 5 µl/min. During this injection the cell was heated to 70° C. for several minutes via a platinum heating electrode within the flow cell and allowed to cool to 25° C. The injection was then continued for a further ten minutes. Once the injection was complete, flow buffer was flushed continuously through the system at a flow rate of 500 µl/min. After 10 minutes the sequencing reaction was initiated by injection of 0.4 mM dATP (8 µl) into the buffer at a flow rate of 500 µl/min. One second after commencing the injection a series of CCD images was recorded at maximum frame rate (30 frames per second) and the image containing the highest signal intensity stored. The complementary nucleotide dCTP was then injected at 0.4 mM at the further CCD images stored one second after injection.

Figure 1B:

The complementary nucleotide gave a strong signal (FIG. 1a) in comparison to the non-complementary nucleotide (FIG. 1b) when imaged in a "time-resolved" manner.

(iii) optionally repeating (i) and (ii) with additional nucleotides, to thereby identify the sequence of the target polynucleotide.

2. The method according to claim 1, wherein (i) and (ii) are carried out with each of the different nucleotides in turn, until incorporation is detected.

3. The method according to claim 1, wherein the target polynucleotide is immobilized on a support material.

4. The method according to claim 1, wherein a plurality of target polynucleotides is immobilized on a support material.

5. The method according to claim 1, wherein (ii) is carried out by measuring applied radiation.

6. The method according to claim 1, wherein (ii) is carried out by measuring raman scattering.

7. The method according to claim 1, wherein (ii) is carried out by applying a surface electromagnetic wave.

8. The method according to claim 7, wherein the surface electromagnetic wave is a surface plasmon wave.

9. The method according to claim 1, wherein detection is carried out by measurement of a surface electromagnetic wave.

10. The method according to claim 1, wherein the polymerase comprises a detectable label attached thereto.

11. The method according to claim 10, wherein the label is a fluorophore.

12. The method according to claim 10, wherein the polymerase further comprises an energy donor label or an energy

I claim:

1. A method for identifying the sequence of a target polynucleotide, comprising:
  (i) contacting the target polynucleotide with a polymerase enzyme and a nucleotide selected from the group consisting of A, T (U), G, and C, under conditions suitable for the polymerase reaction to proceed;
  (ii) measuring the time taken for the polymerase to bind to and subsequently dissociate from the target polynucleotide, to thereby determine whether the polymerase has incorporated the nucleotide onto the target polynucleotide;

acceptor label, and wherein (ii) is carried out by measuring energy transfer between the fluorophore and the energy donor or acceptor.

13. A method for the identification of a mutation in a target polynucleotide, comprising:
  (i) contacting the target polynucleotide with a polymerase enzyme and a nucleotide selected from the group consisting of A, T (U), G, and C, under conditions suitable for the polymerase reaction to proceed;
  (ii) measuring the time taken for the polymerase to bind to and subsequently dissociate from the target polynucleotide, to thereby identify whether the polymerase has incorporated the nucleotide onto the target polynucleotide, and with reference to the native sequence of the target, determine whether a mutation exists.

14. The method according to claim 13, wherein (i) and (ii) are carried out with each of the different nucleotides in turn, until incorporation is detected.

15. The method according to claim 13, wherein a plurality of target polynucleotides is immobilized on a support material.

16. The method according to claim 13, wherein (ii) is carried out by applying a surface electromagnetic wave.

17. The method according to claim 16, wherein the surface electromagnetic wave is a surface plasmon wave.

18. The method according to claim 13, wherein the polymerase comprises a detectable label attached thereto.

19. The method according to claim 18, wherein the polymerase further comprises an energy donor label or an energy acceptor label, and wherein (ii) is carried out by measuring energy transfer between the fluorophore and the energy donor or acceptor.

* * * * *